US008299263B2

(12) United States Patent
Jung et al.

(10) Patent No.: US 8,299,263 B2
(45) Date of Patent: Oct. 30, 2012

(54) N-HETEROCYCLIC CARBENE-AMIDO PALLADIUM(II) CATALYSTS AND METHOD OF USE THEREOF

(75) Inventors: Kyung Woon Jung, Fullerton, CA (US); Kyung Soo Yoo, Fullerton, CA (US); Satoshi Sakaguchi, Hyogo (JP); Chan Phil Park, Chunnam (KR); Justin O'Neill, Pasadena, CA (US); Joo Ho Lee, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 502 days.

(21) Appl. No.: 12/512,747

(22) Filed: Jul. 30, 2009

(65) Prior Publication Data

US 2010/0036131 A1 Feb. 11, 2010

Related U.S. Application Data (60) Provisional application No. 61/084,723, filed on Jul. 30, 2008.

(51) Int. Cl.
*C07F 15/00* (2006.01)
(52) U.S. Cl. ..................................... 548/103
(58) Field of Classification Search ............ 548/103
See application file for complete search history.

(56) References Cited

OTHER PUBLICATIONS

Sakaguchi et al. "Chiral benzimidazolin-2-ylidene Pd(II) complex for intermolecular asymmetric oxidative Heck-type reaction of arylboronic acids with alkenes" ACS National Meeting, Boston, MA, Aug. 19-23, 2007, abstract and poster.*
Kantchev, E.A.B. et al. 2007. Palladium Complexes of N-Heterocyclic Carbenes as Catalysts for Cross-Coupling Reactions-A Synthetic Chemist's Perspective. Angewandte Chemie International Edition, vol. 46, pp. 2768-2813.
Rosner, T. et al. 2001. Kinetic Studies of Heck Coupling Reactions Using Palladacycle Catalysts: Experimental and Kinetic Modeling of the Role of Dimer Species. Journal of the American Chemical Society, vol. 123, pp. 1848-1855.
Rothenberg, G. et al. 2004. Detailed Mechanistic Studies Using in situ Spectroscopic Analysis: A Look at Little-Known Regions of the Heck Reaction. Advanced Synthesis & Catalysis, vol. 346, pp. 467-473.
Sakaguchi, S. et al. 2008. Chiral Palladium(II) Complexes Possessing a Tridentate N-Heterocyclic Carbene Amidate Alkoxide Ligand: Access to Oxygen-Bridging Dimer Structures. Angewandte Chemie International Edition, vol. 47, pp. 9326-9329.
Santos, L.L. et al. 2003. C-H Bond Activation Reactions by TpMe2Ir(III) Centres. Generation of Fischer-Type Carbenes and Development of a Catalytic System for H/D Exchange. New Journal of Chemistry, vol. 27, pp. 107-113.
Sato, Y. et al. 2003. Pd-Catalyzed Allylic Substitution Using Nucleophilic N-Heterocyclic Carbene as a Ligand. Organic Letters, vol. 5, No. 1, pp. 31-33.

Scott, N.M. et al. 2005. Stabilization of Organometallic Species Achieved by the Use of N-Heterocyclic Carbene (NHC) Ligands. European Journal of Inorganic Chemistry 2005, pp. 1815-1828.
Shen, C. et al. 2000. A Bimetallic System for the Catalytic Hydroxylation of Remote Primary C-H Bonds in Functionalized Organics Using Dioxygen. Journal of the American Chemical Society, vol. 122, pp. 4029-4031.
Shilov, A.E., et al. 1997. Activation of C-H Bonds by Metal Complexes. Chemistry Reviews, vol. 97, pp. 2879-2932.
Sigman, M.S. et al. 2006. Ligand-Modulated Palladium-Catalyzed Aerobic Alcohol Oxidations. Accounts of Chemical Research, vol. 39, No. 3, pp. 221-229.
Song, D. et al. 2004. Cyclometalated Tridentate C-N-N Ligands with an Amine or Amido Donor in Platinum(II) and Palladium(II) Complexes and a Novel Potassium Alkoxide Aggregate. Organometallics, vol. 23, pp. 4406-4413.
Steinhoff, B.A. et al. 2002. Mechanistic Study of Alcohol Oxidation by the Pd(OAc)2/02/DMSO Catalyst System and Implications for the Development of Improved Aerobic Oxidation Catalysts. Journal of the American Chemical Society, vol. 124, pp. 766-767.
Strassner, T. et al. 2004. The counterion influence on the CH-activation of methane by palladium(II) biscarbene complexes—structures, reactivity and DFT calculations. Journal of Organometallic Chemistry, vol. 689, pp. 1418-1424.
Trost, B.M. et al. 2006. Catalytic Enantioselective Construction of All-Carbon Quaternary Stereocenters. Synthesis, Jan. 13, 2006, No. 3, pp. 369-396.
Van Strijdonck, G.P.F. et al. 1999. Fast Palladium Catalyzed Arylation of Alkenes Using Bulky Monodentate Phosphorus Ligands. European Journal of Inorganic Chemistry 1999, pp. 1073-1076.
Wang, H.M.J. et al. 1998. Facile Synthesis of Silver(I)-Carbene Complexes. Useful Carbene Transfer Agents. Organometallics, vol. 17, pp. 972-975.
Warmuth, R. et al. 2001. Enantioselective Synthesis of Benzocyclic alpha,alpha-dialkyl-Amino Acids: New Insight into the Solvent Dependent Stereoselectivity of the TMSCN Addition to Phenylglycinol Derived Imines. Tetrahedron, vol. 57, pp. 6383-6397.
Wong-Foy, A.G. et al. 2003. Alkane C-H Activation and Catalysis by an O-Donor Ligated Iridium Complex. Journal of the American Chemical Society, vol. 125, pp. 14292-14293.
Yonehara, K. et al. 2000. Palladium-Catalyzed Asymmetric Intermolecular Arylation of Cyclic or Acyclic Alkenes Using Phosphinite-Oxazoline Ligands Derived from D-Glucosamine. Journal of Organometallic Chemistry, vol. 603, pp. 40-49.
Yoo, K.S. et al. 2006. Oxidative Palladium(II) Catalysis: A Highly Efficient and Chemoselective Cross-Coupling Method for Carbon-Carbon Bond Formation under Base-Free and Nitrogenous-Ligand Conditions. Journal of the American Chemical Society, vol. 128, pp. 16384-16393.
Yoo, K.S. et al. 2007. Asymmetric Intermolecular Heck-Type Reaction of Acyclic Alkenes via Oxidative Palladium(II) Catalysis. Organic Letters, vol. 9, No. 20, pp. 3933-3935.

(Continued)

*Primary Examiner* — Joseph Kosack
(74) *Attorney, Agent, or Firm* — McDermott Will & Emery LLP (57) ABSTRACT

A new N-heterocyclic catalyst system which contains N-heterocyclic carbene and amido as ligands, which are strongly bound to a palladium metal. Another heteroatom functionality can be used as a third ligand L. The NHC-amidate ligand system is unique in structure, and shows excellent reactivities in a number of chemical reactions. The chemical reactions include carbon-carbon and carbon-heteroatom (oxygen and nitrogen) bond formations, and oxidation reactions of saturated carbon chemicals via C—H activation.

18 Claims, No Drawings

OTHER PUBLICATIONS

Zerella, M. et al. 2006. Methane Oxidation to Acetic Acid Catalyzed by Pd2+ Cations in the Presence of Oxygen. Journal of Catalysis, vol. 237, pp. 111-117.

Zhang, W. et al. 2006. Bisoxazoline Ligands with an Axial-Unfixed Biaryl Backbone: The Effects of the Biaryl Backbone and the Substituent at Oxazoline Ring on Cu-Catalyzed Asymmetric Cyclopropanation. Tetrahedron: Asymmetry, vol. 17, pp. 767-777.

Adamo, C. et al. 2006. Mechanism of the Palladium-Catalyzed Homocoupling of Arylboronic Acids: Key Involvement of a Palladium Peroxo Complex. Journal of the American Chemical Society 2006, vol. 128, pp. 6829-6836.

Akiyama, K. et al. 2005. Enantioselective Heck-Type Reaction Catalyzed by tropos-Pd(II) Complex with Chiraphos Ligand. Advanced Synthesis & Catalysis, 2005, vol, 347, pp. 1569-1575.

Akiyama, K. et al. 2007. Pd(II)—Catalyzed Enantioselective Intramolecular Heck-Type Reaction to Construct Chiral Sulfonamide Rings. Heterocycles 2007, vol. 74, pp. 827-834.

Albano, V.G. et al. 2006. Synthesis and Crystallographic Characterization of Chiral Bis-oxazoline-amides. Fine-Tunable Ligands for Pd-Catalyzed Asymmetric Alkylations. Journal of Organic Chemistry, vol. 71, pp. 6451-6458.

Arakawa, H. et al. 2001. Catalysis Research of Relevance to Carbon Management: Progress, Challenges, and Opportunities. Chemistry Reviews, vol. 101, pp. 953-996.

Arndtsen, B.A., et al. 1995. Selective Intermolecular Carbon-Hydrogen Bond Activation by Synthetic Metal Complexes in Homogeneous Solution. Accounts of Chemical Research, vol. 28, pp. 154-162.

Augustine, R.L. et al. 1985. Site Specificity in the Room Temperature Deuterium Exchange of Cyclopentane over Platinum/CPG Catalysts. Langmuir, vol. 1, pp. 262-264.

Benaglia, M. et al. 2005. Steric and Electronic Tuning of Chiral Bis(oxazoline) Ligands with 3,3'-Bithiophene Backbone. Journal of Organic Chemistry, vol. 70, pp. 7488-7495.

Bolm, C. et al. 1991. Synthesis of Optically Active Bis(2-oxazolines): Crystal Structure of a 1,2-Bis(2-oxazolinyl) benzene ZnCl2 Complex. Chemische Berichte, vol. 124, pp. 1173-1180.

Bonnet, L.G. et al. 2003. Synthesis of New Chiral N-Heterocyclic Carbene-Imine Ligands and Their Application to an Asymmetric Allylic Alkylation Reaction. Organometallics, vol. 22, pp. 4187-4189.

Bourissou, D. et al. 2000. Stable Carbenes. Chemistry Reviews vol. 100, pp. 39-91.

César, V. et al. 2004. Chiral N-heterocyclic carbenes as stereodirecting ligands in asymmetric catalysis. Chem. Soc. Rev., vol. 33, pp. 619-636.

Cornejo, A. et al. 2002. The First Immobilization of Pyridine-bis(oxazoline) Chiral Ligands. Organic Letters, vol. 4, No. 22, pp. 3927-3930.

Crabtree, R.H. 1995. Aspects of Methane Chemistry. Chemistry Reviews, vol. 95, pp. 987-1007.

Crabtree, R.H. 2001. Alkane C-H Activation and Functionalization with Homogeneous Transition Metal Catalysts: a Century of Progress—a New Millennium in Prospect. Journal of the Chemical Society Dalton Transactions, pp. 2437-2450.

Dodd, D.W. et al. 2006. Model Intermolecular Asymmetric Heck Reactions Catalyzed by Chiral Pyridyloxazoline Palladium(II) Complexes. Inorganica Chimica Acta, vol. 359, pp. 2850-2858.

Douthwaite, R.E. 2007. Metal-Mediated Asymmetric Alkylation Using Chiral N-Heterocyclic Carbenes Derived from Chiral Amines. Coordination Chemistry Reviews, vol. 251, pp. 702-717.

Duthaler, R.O. 1994. Recent Developments in the Stereoselective Synthesis of alpha-Aminoacids. Tetrahedron, vol. 50, No. 6, pp. 1539-1650.

Gade, L.H. et al. 2007. Chiral N-Heterocyclic Carbenes as Stereodirecting Ligands in Asymmetric Catalysis. Topics in Organometallic Chemistry, vol. 21, pp. 117-157.

Goeppert, A. et al. 2002. Methane Activation and Oxidation in Sulfuric Acid. Chemistry A European Journal, vol. 8, No. 14, pp. 3277-3283.

Golden, J.T. et al. 2001. Exceptionally Low-Temperature Carbon-Hydrogen/Carbon-Deuterium Exchange Reactions of Organic and Organometallic Compounds Catalyzed by the Cp*(PMe3)IrH(ClCH2Cl)+ Cation. Journal of the American Chemical Society, vol. 123, pp. 5837-5838.

Goldman, A.S., et al. 2004. Organometallic C-H Bond Activation: An Introduction, in Activation and Functionalization of C-H Bonds, Oxford University Press, Washington D.C., pp. 1-43.

Gutierrez-Puebla, E. et al. Synthesis and Properties of TpMe2IrH4 and TpMe2IrH3(SiEt3): Ir(V) Polyhydride Species with C3v Geometry. Journal of the American Chemical Society, vol. 121, pp. 346-354, 1999.

Hermann, W.A. et al. 1998. Chiral Oxazoline/Imidazoline-2-ylidene Complexes. Organometallics, vol. 17, pp. 2162-2168.

Herrmann, W.A. 2002. N-Heterocyclic Carbenes: A New Concept in Organometallic Catalysis. Angewandte Chemie International Edition, vol. 41, pp. 1290-1309.

Hodgson, R. et al. 2005. Synthesis and Asymmetric Catalytic Application of Chiral Imidazolium—Phosphines Derived from (1R,2R)-trans-Diaminocyclohexane. Journal of Organometallic Chemistry, vol. 690, pp. 5822-5831.

Hou, D.-R. et al. 1999. JM-PHOS Ligands: Second-Generation Phosphine Oxazolines for Asymmetric Catalysis. Organic Letters vol. 1, pp. 1745-1747.

Hou, D.-R. et al. 2001. New, Optically Active Phosphine Oxazoline (JM-PHOS) Ligands: Syntheses and Applications in Allylation Reactions. Journal of Organic Chemistry, vol. 66, pp. 206-215.

Jones, W.D. 2000. Hydrocarbon Chemistry: Enhanced: Conquering the Carbon-Hydrogen Bond. Science, vol. 287, pp. 1942-1943 (plus 3 pages of hypernotes).

Kakiuchi, F. et al. 1999. Activation of C-H Bonds: Catalytic Reactions. Topics in Organometallic Chemistry, vol. 3, pp. 47-79.

Klei, S.R. et al. 2002. Iridium-Catalyzed H/D Exchange into Organic Compounds in Water. Journal of the American Chemical Society, vol. 124, No. 10, pp. 2092-2093.

Labinger, J.A. et al. 2002. Understanding and exploiting C-H bond activation. Nature, vol. 417, pp. 507-514.

Lee, J.C., Jr. et al. 1995. An Unusual Coordination Mode for Amides: Lone-Pair Binding via Nitrogen. Inorganic Chemistry, vol. 34, pp. 6295-6301.

Lee, J.H. et al. 2009. An Air/Water-Stable Tridentate N-Heterocyclic Carbene-Palladium(II) Complex: Catalytic C-H Activation of Hydrocarbons via Hydrogen/Deuterium Exchange Process in Deuterium Oxide. Advanced Synthesis & Catalysis, vol. 351, pp. 563-568.

Lee, S. et al. 2001. Improved Catalysts for the Palladium-Catalyzed Synthesis of Oxindoles by Amide alpha-Arylation. Rate Acceleration, Use of Aryl Chloride Substrates, and a New Carbene Ligand for Asymmetric Transformations. Journal of Organic Chemistry, vol. 66, pp. 3402-3415.

Lei, G.-D. et al. 1993. H/D Exchange of Cyclopentane on Pt/Mordenites: Probing for Monoatomic Pt Sites. Journal of Catalysis, vol. 140, pp. 601-611.

Lin, I.J.B. et al. 2007. Preparation and Application of N-Heterocyclic Carbene Complexes of Ag(I). Coordination Chemistry Reviews, vol. 251, pp. 642-670.

Luecke, H.F. et al. 1996. Synthesis of Fischer Carbene Complexes of Iridium by C-H Bond Activation of Methyl and Cyclic Ethers: Evidence for Reversible alpha-Hydrogen Migration. Journal of the American Chemical Society, vol. 118, pp. 2517-2518.

Lunsford, J.H. 2000. Catalytic Conversion of Methane to More Useful Chemicals and Fuels: a Challenge for the 21st Century. Catalysis Today, vol. 63, pp. 165-174.

Matsumoto, K. et al. 2005. Multicomponent Strecker Reaction under High Pressure. Helvetica Chimica Acta, vol. 88, pp. 1734-1753.

Muehlhofer, M. et al. 2002. New Catalyst Systems for the Catalytic Conversion of Methane into Methanol. Angewandte Chemie International Edition, vol. 41, No. 10, pp. 1745-1747.

Murata, K. et al. 2002. Deprotonation of Organic Compounds Bearing Acid Protons Promoted by Metal Amido Complexes with Chiral Diamine Ligands Leading to New Organometallic Compounds. Organometallics, vol. 21, pp. 253-255.

Penn, L. et al. 2007. Enantio- and Regioselective Heck-Type Reaction of Arylboronic Acids with 2,3-Dihydrofuran. Journal of Organic Chemistry, vol. 72, pp. 3875-3879.

Periana, R.A. et al. 2003. Catalytic, Oxidative Condensation of CH4 to CH3COOH in One Step via CH Activation. Science, vol. 301, pp. 814-818.

Periana, R.A., et al. 2004. Perspectives on Some Challenges and Approaches for Developing the Next Generation of Selective, Low Temperature, Oxidation Catalysts for Alkane Hydroxylation Based on the CH Activation Reaction. Journal of Molecular Catalysis A: Chemical, vol. 220, pp. 7-25.

Periana, R.A. et al. 2005. Homogeneous, catalytic, oxidative coupling of methane to acetic acid in one step. Topics in Catalysis, vol. 32, Nos. 3-4, Mar. 3-4, 2005, pp. 169-174.

Perry, M.C. et al. 2003. Chiral N-heterocyclic Carbene-Transition Metal Complexes in Asymmetric Catalysis. Tetrahedron: Asymmetry, vol. 14, pp. 951-961.

Perry, M.C. et al. 2003. Optically Active Iridium Imidazol-2-ylidene-oxazoline Complexes: Preparation and Use in Asymmetric Hydrogenation of Arylalkenes. Journal of the American Chemical Society vol. 125, pp. 113-123.

Powell, M.T. et al. 2001. Chiral Imidazolylidine Ligands for Asymmetric Hydrogenation of Aryl Alkenes. Journal of the American Chemical Society vol. 123, pp. 8878-8879.

Ren, L. et al. 2004. Chiral Bidentate N-Heterocyclic Carbene Complexes of Rh and Pd. Canadian Journal of Chemistry, vol. 82, pp. 1781-1787.

\* cited by examiner

N-HETEROCYCLIC CARBENE-AMIDO PALLADIUM(II) CATALYSTS AND METHOD OF USE THEREOF

CROSS-REFERENCE TO RELATED APPLICATION(S)

This application is based upon and claims priority to U.S. Provisional Patent Application No. 61/084,723, entitled "N-Heterocyclic Carbene Palladium(II) Catalysts and Method of Use Thereof in C—C Bond formation and C—H Activation" filed Jul. 30, 2008.

The entire content of the application identified above is incorporated herein by reference.

STATEMENT REGARDING FEDERALLY SPONSORED RESEARCH

This invention was made with Government support under Contract No. R01 GM 071495 awarded by the National Institutes of Health. The Government has certain rights in the invention.

BACKGROUND

1. Technical Field

This disclosure relates to the use of novel catalysts in various chemical reactions. Specifically, the disclosure is directed to N-Heterocyclic Carbene-Amido Palladium(II) catalysts and use of these catalysts in organic synthesis.

2. Description of Related Art

Catalysts are one of the most important classes of compounds in nature. Catalysts have the capability of significantly increasing reaction rates of a variety of compounds. Estimates are that 90% of all commercially produced chemical products involve catalysts at some stage in the process of their manufacture.

Palladium catalyzed coupling reactions are extremely powerful and versatile synthetic methods for carbon-carbon and carbon-heteroatom bond formation. N-heterocyclic carbenes (NHCs) have been employed successfully as ligands to generate a variety of palladium complexes due to their enhanced chemical properties and the strong Pd-NHC σ-bonding which contributes to the high stability of the active species compared with traditional phosphane ligands.

Lee and Hartwig have prepared monodentate NHC ligands with a bulky chiral terpene group attached to the nitrogen atoms for use in asymmetric intramolecular α-arylation. However, these enantioselective transformations employing a monodentate ligand can be cumbersome since various inactive palladium-ligand complexes, such as a trans-conformation, may be prepared.

NHC ligands are also known to have enhanced σ-donor coordination which allow for stable catalysts for C—H activation. However, most examples refer to intramolecular processes, as intermolecular or catalytic examples are rare. In particular, aqueous conditions for organometallic complexes are not developed because of the vulnerability of metal-carbon bonds, thereby limiting their roles in innocent auxiliary ligand sets or transient ligands in catalytic reactions. In recent years, a substantial number of metal complexes that are able to selectively activate C—H bonds under mild conditions have been discovered. However, practical catalysts for C—H bond functionalization have been elusive, partially due to the fact that the C—H bond activation is often inhibited by water or by the alcohol product eliminated from the metal complex during the reaction.

SUMMARY

In order to overcome the problems discussed above, the present disclosure is directed toward a new NHC catalyst system as shown in General Formula 1. These catalysts contain N-heterocyclic carbene and amido groups as ligands, which are strongly bound to the palladium metal. Another heteroatom functionality can be used as a third ligand L in another embodiment of the present disclosure. The NHC-amidate ligand system is unique in structure, and it shows excellent reactivities in a number of chemical reactions.

general formula I

Figure 1:
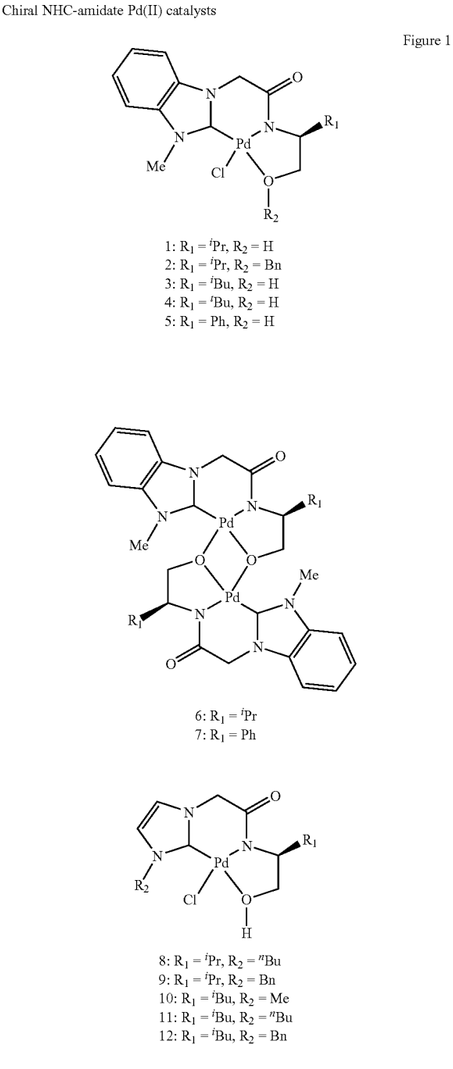

The structure of general formula I, where $R_1$ and $R_5$ may be the same or different and are selected from the group consisting of H, or alkyl, aryl, or aralkyl, each of which have 1 to 10 carbon atoms, and may optionally contain one or more heteroatoms; $R_2$ is selected from the group consisting of H, or alkyl, aryl, or aralkyl, each of which have 1 to 10 carbon atoms, or optionally forms part of a linkage to form a dimer; $R_3$ and $R_4$ is selected from the group consisting of H, or aryl ring of from 4 to 10 carbon atoms; $R_6$ is selected from the group consisting of H, or alkoxy of 1-4 carbon atoms; and L is selected from the group consisting of a halogen, or optionally forms part of a linkage to form a dimer. An example of the dimeric form of general formula I is shown in FIG. 1, compounds 6 and 7.

The catalysts of the present disclosure facilitate a number of chemical reactions including carbon-carbon and carbon-heteroatom (oxygen and nitrogen) bond formations, and oxidation reactions of saturated carbon chemicals via C—H activation. By varying several combinations of functional groups in the ligand design, a high quality library of new tridentate NHC-amidate Pd catalysts for many organic reactions was prepared.

The present disclosure is also directed toward a method of forming new C—C, C—N, C—O bonds, epoxide formation, H/D exchange, formation of α-aminonitrile products containing a quaternary carbon, the direct formation of acetic acid from methane via C—H activation, oxidation, and C—C bond formation. All of these compound classes are catalyzed by the NHC-amidate Pd catalysts of general formula I, or more specifically, of FIGS. 1-2.

These, as well as other components, steps, features, objects, benefits, and advantages, will now become clear from a review of the following detailed description of illustrative embodiments and the claims, or may be learned from the practice of the disclosure. The advantages of the disclosure may be realized and obtained as particularly pointed out in the appended claims.

As will be realized, the present disclosure is capable of other and different embodiments, and its several details are capable of modifications in various obvious respects, all without departing from the disclosure. Accordingly, the description is to be regarded as illustrative in nature, and not as restrictive.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Figure 2:
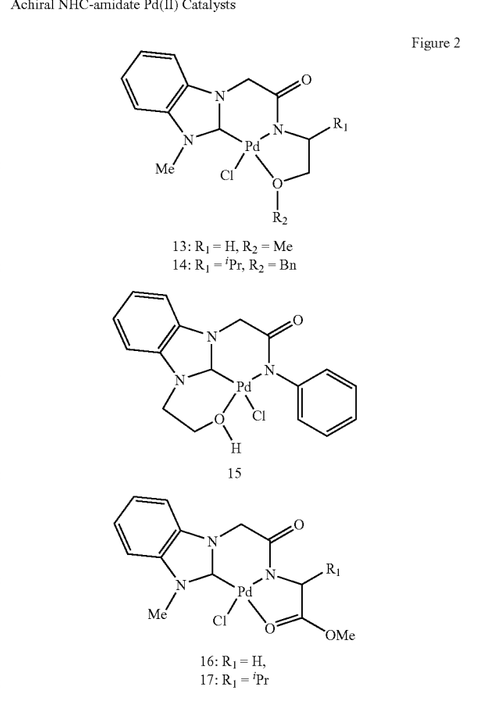

FIGS. 1 and 2 show certain specific catalysts representing individual embodiments of the present disclosure. FIG. 1 shows structures of chiral NHC-amidate Pd(II) catalysts and FIG. 2 are structures of achiral NHC-amidate Pd(II) catalysts.

Chiral NHC-amidate Pd(II) catalysts

Figure 1

1: $R_1 = {}^iPr$, $R_2 = H$
2: $R_1 = {}^iPr$, $R_2 = Bn$
3: $R_1 = {}^iBu$, $R_2 = H$
4: $R_1 = {}^iBu$, $R_2 = H$
5: $R_1 = Ph$, $R_2 = H$

6: $R_1 = {}^iPr$
7: $R_1 = Ph$

8: $R_1 = {}^iPr$, $R_2 = {}^nBu$
9: $R_1 = {}^iPr$, $R_2 = Bn$
10: $R_1 = {}^iBu$, $R_2 = Me$
11: $R_1 = {}^iBu$, $R_2 = {}^nBu$
12: $R_1 = {}^iBu$, $R_2 = Bn$

Achiral NHC-amidate Pd(II) Catalysts

Figure 2

13: $R_1 = H$, $R_2 = Me$
14: $R_1 = {}^iPr$, $R_2 = Bn$

15

16: $R_1 = H$,
17: $R_1 = {}^iPr$

Synthesis of N-Heterocyclic Carbene-Amidate Pd(II) Catalysts

Scheme 1 shows a general method for synthesizing chiral NHC-amidate Pd(II) catalysts as complexes 1-5. Compounds A were prepared from chiral β-amino alcohols, derived from chiral amino acids. Bromoacetylation of compounds A was followed by amide formation and N-alkylation with benzimidazole to yield B. The benzimidazole salts C were obtained by allowing B to react with $CH_3I$ in THF. For the coordination of NHC's to palladium, metal exchange was carried out through a silver NHC complex. N-Methyl iodide salts C were reacted with $Ag_2O$ to give silver NHC complexes, and subsequent treatment of the silver compounds with $PdCl_2(CH_3CN)_2$ in $CH_3CN$ provided the desired complexes 1-5, respectively. In Scheme 1, $R_1$ and $R_2$ may be the same or different and are from the group selected from hydrogen, or alkyl, aryl or aralkyl group, each of which have 1 to 10 carbon atoms. Optionally, the alkyl, aryl or aralkyl group contains one or more heteroatoms.

Scheme 1

A

1: $R_1 = {}^iPr$, $R_2 = H$
2: $R_1 = {}^iPr$, $R_2 = Bn$
3: $R_1 = {}^iBu$, $R_2 = H$
4: $R_1 = {}^tBu$, $R_2 = H$
5: $R_1 = Ph$, $R_2 = H$

6: $R_1 = {}^iPr$
7: $R_1 = Ph$

Scheme 3 shows a general synthetic route to complexes 8-12 of FIG. 1. Imidazoline NHC ligand precursor G was synthesized by N-alkylation with chlorine compound E and N-alkyl imidazole F under reflux condition in dioxane for 16 hours. Chlorine compound E was prepared from amidation between chiral amino alcohol D and chloroacetyl chloride in the presence of triethyl amine as base. Then, their corresponding NHC-Pd complexes 8-12 were provided by treatment with half an equivalent of $Ag_2O$ and one equivalent of $PdCl_2(CH_3CN)_2$ sequentially in $CH_3CN$ solution at room temperature. In Scheme 3, $R_1$ and $R_2$ may be the same or different and are from the group selected from hydrogen, or alkyl, aryl or aralkyl group, each of which have 1 to 10 carbon atoms. Optionally, the alkyl, aryl or aralkyl group contains one or more heteroatoms.

Scheme 2 shows the formation of a group of dimeric chiral NHC-amidate Pd(II) catalysts of another embodiment of the present disclosure. Dehydrohalogenation of 1 and 5 in the presence of $K_2CO_3$ produced NHC-Pd(II) complexes 6 and 7 in high conversion yields, respectively. Only one isomer of each of the dimeric compounds was detected in solution by $^1$H-NMR spectroscopic analysis. In Scheme 2, $R_1$ is from the group selected from hydrogen, or alkyl, aryl or aralkyl group, each of which have 1 to 10 carbon atoms. Optionally, the alkyl, aryl or aralkyl group contains one or more heteroatoms.

8~12

Achiral NHC-Pd(II) complexes 13 and 14 were prepared in the same manners as Scheme 1.

Scheme 4

13: $R_1$ = H, $R_2$ = Me
14: $R_1$ = $^i$Pr, $R_2$ = Bn

Scheme 5 shows the formation of a catalyst of another embodiment of the present disclosure. A pincer-type tridentate ligand system, the alkoxy-NHC-amidate ligand/palladium complex 15, was prepared from amide compound H, derived from aniline and bromoacetyl bromide (Scheme 5). By means of N-alkylation with benzimidazole and compound H, the benzimidazole-amide adduct was obtained in DMF solution, which after second N-alkylation with iodoethanol gave the iodine salt I. Subsequently, construction of alkoxy-NHC-amidate ligand/palladium complex 15 was successfully accomplished by treatment with half an equivalent of $Ag_2O$ and one equivalent of $PdCl_2(CH_3CN)_2$ sequentially in $CH_3CN$ solution at room temperature.

Scheme 5

15

The preparation of catalysts according to another embodiment of the present disclosure was carried out as illustrated in Scheme 6. Treatment of J, derived from the amidation of valine methyl ester (or glycine methyl ester) and bromoacetyl bromide, with benzimidazole in the presence of KOH in DMF provided compound K efficiently. The amido ester-substituted benzimidazolium iodine salt L was then obtained by allowing K to react with $CH_3I$ in refluxing THF. For coordination of L as an NHC to palladium, compound L was reacted with $Ag_2O$ in dichloromethane at room temperature for 3 h, and then the solvent was filtered under reduced pressure to give the silver NHC complex as a light gray color solid. This reaction could be carried out without any purification of the intermediate. Subsequent treatment of the silver compound with $PdCl_2(CH_3CN)_2$ in $CH_3CN$ at room temperature for 3 h afforded palladium complexes 16 and 17 in good yields, respectively. In Scheme 6, $R_1$ is from the group selected from hydrogen, or alkyl, aryl or aralkyl group, each of which have 1 to 10 carbon atoms. Optionally, the alkyl, aryl or aralkyl group contains one or more heteroatoms.

Scheme 6

EXAMPLES

The components, steps, features, objects, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Example 1

C—C Bond Formation (Asymmetric Boron-Heck Type Reactions

In Example 1, carbon-carbon bond formation by enantioselective oxidative boron-Heck type cross-couplings of arylboronic acid and olefins is promoted. Particularly, chiral dimeric tridentate NHC-amidate-alkoxide Pd(II) complexes, 6 and 7, effected asymmetric oxidative boron Heck-type reactions of arylboronic acids with both acyclic (equation 1) and cyclic (equation 2) alkenes at room temperature to afford the corresponding coupling products with high enantioselectivities. The representative examples for these cross-coupling reactions to offer high enantioselectivities unprecedented in intermolecular Heck-type couplings are shown in Tables 1 and 2.

TABLE 1

Asymmetric oxidative Heck reaction using Pd-ligand complexes 6 and 7[a]

(1)

| Entry | ArB(OH)$_2$ | Alkene | Cat. | Product[b] | Conf.[c] |
|---|---|---|---|---|---|
| 1 | phenyl-B(OH)$_2$ | methyl (E)-2-methylbut-2-enoate | 6 | 49%, 91% ee | R |
| 2 | 2-naphthyl-B(OH)$_2$ | | 6 | 61%, 92% ee | — |
| 3 | 4-methoxyphenyl-B(OH)$_2$ | | 6 | 51%, 91% ee | R |
| 4 | 4-(dimethylamino)phenyl-B(OH)$_2$ | | 6 | 52%, 91% ee | R |

TABLE 1-continued

Asymmetric oxidative Heck reaction using Pd-ligand complexes 6 and 7[a]

(1)

| Entry | ArB(OH)₂ | Alkene | Cat. | Product[b] | Conf.[c] |
|---|---|---|---|---|---|
| 5 |  | | 6 | 42%, 89% ee | R |
| 6 |  | | 6 | 29%, 87% ee | — |
| 7 |  |  | 6 | 41%, 88% ee | — |
| 8 |  |  | 6 | 45%, 87% ee | R |
| 9 |  | | 6 | 41%, 88% ee | — |
| 10 |  |  | 7 | 33%, 90% ee | R |
| 11 |  | | 7 | 29%, 94% ee | — |

[a]The reaction was carried out using arylboronic acid (0.5 mmol), alkene (1.5 mmol) in the presence of catalyst 6 (0.02 mmol).
[b]Isolated yields based on arylboronic acids. For determination of enantiomeric excess, see the supporting information.
[c]Absolute configuration.

TABLE 2

Asymmetric oxidative Heck reaction using Pd-ligand complexes 6 and 7[a]

(2)

| Entry | ArB(OH)₂ | Alkene | Cat. | Product (yield)[b] |
|---|---|---|---|---|
| 1 | 2-methylphenyl-B(OH)₂ | 1-acetylcyclopentene | 6 | 44%, 87% ee |
| 2 | 4-methoxyphenyl-B(OH)₂ | 1-acetylcyclopentene | 6 | 54%, 81% ee |
| 3 | 4-(dimethylamino)phenyl-B(OH)₂ | 1-acetylcyclopentene | 6 | 51%, 82% ee |
| 4 | 4-chlorophenyl-B(OH)₂ | 1-acetylcyclopentene | 6 | 57%, 91% ee |
| 5 | phenyl-B(OH)₂ | methyl cyclopentene-1-carboxylate | 6 | 62%, 83% ee |
| 6 | 4-methoxyphenyl-B(OH)₂ | methyl cyclopentene-1-carboxylate | 6 | 56%, 85% ee |
| 7 | 4-chlorophenyl-B(OH)₂ | methyl cyclopentene-1-carboxylate | 6 | 48%, 82% ee |
| 8 | phenyl-B(OH)₂ | 1-acetylcyclopentene | 7 | 52%, 84% ee |

[a]The reaction was carried out using arylboronic acid (0.5 mmol), alkene (1.5 mmol) in the presence of catalyst 3 (0.02 mmol).
[b]Isolated yields based on arylboronic acids. For determination of enantiomeric excess, see the supporting information.

Example 2

C—O Bond Formation (Dioxygenation and Epoxidation)

In Example 2, catalytic olefin dioxygenation and epoxidation by chiral NHC-amidate Pd(II) complex 2 was examined to give vicinal oxidation products and epoxides. This method is an attractive approach for making valuable products from simple and readily available olefins. As shown in Table 3, conditions for diacetoxylation of olefins allowed for efficient conversion of the olefin starting material to the product. Especially, allylic acid was oxidized to provide chiral acetoxy γ-lactone in excellent yields, having moderate enantioselectivity (69% ee, entry 1).

TABLE 3

Asymmetric diacetoxylation reaction by chiral Pd-ligand 2[a]

(3)

| Entry | Sbstrate | Product (yield %) |
|---|---|---|
| 1 | 3-butenoic acid | acetoxy γ-lactone, 91 (69% ee) |
| 2 | styrene | 1,2-diacetoxy-1-phenylethane, 86 |
| 3 | allyl cyanide | 2,3-diacetoxybutanenitrile, 93 |

[a]The reaction was carried out using olefin (0.5 mmol) and peracetic acid (1.5 mmol) in the presence of catalyst 2 (0.02 mmol) at 25° C.

In addition, epoxidation of the olefin was carried out under acetic peracid or hydrogen peroxide as the oxidant for 4 hours at 0° C. Although some reaction conversion was modest compared with conditions used by Sharpless and Shi, this result was encouraging enough to embark on further studies of more effective NHC-amidate Pd(II) complexes and reaction conditions. In particular, an epoxidation of (E)-stilbene was explored as the representative asymmetric reaction to provide (E)-(+)-stilbene oxide in 90% yield and 81% enantiomeric excess (Table 4, entry 1).

TABLE 4

Asymmetric epoxidation reaction by chiral Pd-ligand 2[a]

| Entry | Sbstrate | Product (yield %) | |
|---|---|---|---|
| 1 | | | 90 (81% ee) |
| | | trans | |
| 2 | | | 51 |
| | | trans | |
| 3 | | | 30 |

[a]The reaction was carried out using olefin (0.5 mmol) and peracetic acid (1.0 mmol) in the presence of catalyst 2 (0.02 mmol) at 0° C.

Example 3

C—N Bond Formation (Hydroamination)

Hydroamination is of particular significance among various synthetic routes to directly form new C—N bonds. To address the reactivity and selectivity, Example 3 shows representative reactions by using NHC-amidate Pd(II) complex 13 which confirms that the catalyst effects hydroamination (equation 5) significantly to provide amines regioselectively (more substituted sp$^2$ carbon site) in modest yields. As shown in Table 5, hydroamination was effectively facilitated with arenyl and allylic olefin.

TABLE 5

Hydroamination reaction using Pd-ligand 13[a]

| Entry | R | $R_1$ | $R_2$ | Product (yield %)[b] |
|---|---|---|---|---|
| 1 | Ph | H | H | 65 |
| 2 | Ph | H | Me | 50 |
| 3 | Ph | Me | H | 95 |
| 4 | Bn | H | H | 31 |

[a]The reaction was carried out using arylboronic acid (0.5 mmol), alkene (1.5 mmol) in the presence of catalyst 13 (0.02 mmol).
[b]Yields determined by $^1$H-NMR using DMF as a internal standard.

Example 4

H/D Exchange Via C—H Activation

In aqueous solution, tridentate NHC-Pd(II) complex 13 showed high ability for C—H activation of various hydrocarbons under mild conditions. As shown in Table 6, the feasibility of H/D exchange reaction of various organic substrates (cyclohexane, cyclopentane, tetrahydrofuran, diethyl ether, acetone and toluene) in the presence of NHC-Pd(II) complex 13 was investigated. In general, effective multiple deuterium incorporation into the alkyl C—H bond was observed with $D_2O$ as both the solvent and deuterium source. Table 6 lists the organic substrates examined and their corresponding extents of deuterium incorporation.

TABLE 6

H/D exchange of various organic substrates in D₂O by Pd catalyst 13.[a]

| | | | | D conversion (%)[c]/TON[d] | |
|---|---|---|---|---|---|
| Entry | Cat. 13 (μmol) | Substrate[b] | Temp (° C.) | 6 hrs | 22 hrs |
| 1 | 3.86 | cyclohexane | 55 | 81/464 | 93/536 |
| 2 | 3.86 | | 100 | 96/552 | 93/536 |
| 3 | 3.86 | cyclopentane | 55 | 72/399 | 76/422 |
| 4 | 3.86 | | 100 | 96/533 | 97/541 |
| 5 | 3.86 | tetrahydrofuran | 55 | 2/10 | 2/10 |
| 6 | 3.86 | | 100 | 44/222 | 52/267 |
| 7 | 3.86 | diethyl ether | 55 | 0.5/2 | 1/4 |
| 8 | 3.86 | | 100 | 5/25 | 9/43 |
| 9 | 15.40 | | 100 | 27/27 | 46/46 |
| 10 | 3.86 | acetone | 55 | 12/52 | 15/65 |
| 11 | 3.86 | | 100 | 26/1 | 52/218 |
| 12 | 15.40 | | 100 | 55/58 | 63/66 |
| 13 | 3.86 | toluene | 55 | 83/323 | 87/340 |
| 14 | 3.86 | | 100 | 95/369 | 97/379 |

[a]All reactions were performed with Pd complex 13 (μmol) in sealed glass tubes containing D₂O and substrate at 55 and 100° C.
[b]20 μL.
[c]For % D, ¹H NMR spectroscopy was used for analysis.
[d][D conversion × mole of substrate]/[mole of Pd × 100].

In addition, which tested the possibility of direct oxidation of an sp² C—H bond, benzene, was added to the reaction mixture of NHC-Pd catalyst 13 (10 mol %) in hydrogen peroxide solution (equation 6). We detected the oxidation product of benzene via C—H activation to afford phenol as a product.

(6)

Example 5

Three-Component Strecker Reaction of Ketones

In Example 5, NHC-amidate ester Pd(II) complex 17 is shown to be an useful Lewis acid catalyst to promote one-pot multicomponent Strecker reactions for the synthesis of α-aminonitriles. In particular, the reactions involving ketone substrates allowed for the formation of α-aminonitrile products containing a quaternary carbon. In the presence of 17, good reactivity was observed for reactions involving an aromatic amine and ketones with electron-donating (entry 2) substituents, as indicated in Table 7. A bromo-substituent was tolerated as well (entry 3), but the electron-withdrawing nitro group (entry 4) was not a feasible substrate. This suggests that nucleophilic attack of the cyanide source is sensitive to the electronic character of the imine intermediate and becomes more difficult when more strongly electron-withdrawing substituents are present. In general, reactions employing aniline as the amine provided the α-aminonitrile products in better conversion than did those using benzylamine. Again, electron-withdrawing substituents on the ketone substrate were not well-tolerated, although electron-donating (entry 8), and heteroatom (entry 10) substituents provided modest reactivities. One benefit of this methodology is the simplicity of the procedure involved, which often avoided the use of tedious chromatographic purification of products.

TABLE 7

Strecker reactions of various ketones and amines with Pd complex 17.

$$R_1 \overset{O}{\underset{Me}{\|}} + R_2-NH_2 + TMSCN \xrightarrow[CH_2Cl_2, r.t.]{cat.\ 17} R_1 \underset{H}{\overset{NC\ Me}{\underset{|}{C}}} N-R_2$$

(7)

| Entry | Aldehyde | Amine | Product | Conv.(Yield) (%) |
|---|---|---|---|---|
| 1 | 2-acetylnaphthalene | aniline | α-(naphthalen-2-yl)-α-methyl-α-(phenylamino)acetonitrile | 99 (92) |
| 2 | 4'-methoxyacetophenone | aniline | α-(4-methoxyphenyl)-α-methyl-α-(phenylamino)acetonitrile | 86 (74) |
| 3 | 4'-bromoacetophenone | aniline | α-(4-bromophenyl)-α-methyl-α-(phenylamino)acetonitrile | 95 (88) |
| 4 | 4'-nitroacetophenone | aniline | α-(4-nitrophenyl)-α-methyl-α-(phenylamino)acetonitrile | 17 (15) |
| 5 | 3-acetylpyridine | aniline | α-(pyridin-3-yl)-α-methyl-α-(phenylamino)acetonitrile | 44 (40) |
| 6 | 2-acetylfuran | aniline | α-(furan-2-yl)-α-methyl-α-(phenylamino)acetonitrile | 85 (83) |
| 7 | 2-acetylnaphthalene | benzylamine | α-(naphthalen-2-yl)-α-methyl-α-(benzylamino)acetonitrile | 49 (33) |
| 8 | 4'-methoxyacetophenone | benzylamine | α-(4-methoxyphenyl)-α-methyl-α-(benzylamino)acetonitrile | 58 (35) |

TABLE 7-continued

Strecker reactions of various ketones and amines with Pd complex 17.

$$R_1 \overset{O}{\underset{Me}{\|}} + R_2-NH_2 + TMSCN \xrightarrow[CH_2Cl_2, r.t.]{cat. 17} \underset{R_1}{\overset{NC}{\underset{}{}}}\overset{Me}{\underset{N}{\underset{H}{}}}R_2$$

(7)

| Entry | Aldehyde | Amine | Product | Conv.(Yield) (%) |
|---|---|---|---|---|
| 9 | 4-Br-C6H4-C(O)-Me | BnNH2 | 4-Br-C6H4-C(CN)(Me)-NHBn | 62 (55) |
| 10 | 3-pyridyl-C(O)-Me | BnNH2 | 3-pyridyl-C(CN)(Me)-NHBn | 68 (60) | a) To a mixture of palladium catalyst, sodium sulfate (100 mg, 0.7 mmol), ketones (0.2 mmol), and amines (0.52 mmol) in 1 mL CH$_2$Cl$_2$ in Schlenk tube was added dropwise TMSCN (0.4 mmol). The mixture was stirred for 24 hrs at room temperature.
b) Isolated yields.

Example 6

Conversion of Methane to Acetic Acid

Example 6 demonstrates the ability of the NHC-amido Pd(II) complexes to impart high chemo-selectivity and productivity for the direct formation of acetic acid from methane via C—H activation, oxidation, and C—C bond formation. For Example, Table 8 shows the reaction of methane in the presence of HBF$_4$, hydrogen peroxide and designed tridentate NHC-amidate palladium complexes 13 and 14 to form acetic acid.

TABLE 8

Conversion of methane to acetic acid.[a]

$$CH_4 \xrightarrow[H_2O_2, \text{lutidine}]{NHC\text{-}Pd, HBF_4} CH_3COOH$$
(400 psi)   60° C.

(8)

| Entry | Catalyst | H$_2$O$_2$ (μL) | Time (hr) | 2,6-Lutidine (μL) | AcOH (TON)[b] |
|---|---|---|---|---|---|
| 1 | 13 | 40 | 16 | — | 0.1 |
| 2 | 13 | 300 | 16 | — | 1.6 |
| 3 | 13 | 160 | 16 | 57 | 1.8 |
| 4 | 14 | 40 | 16 | — | 0.1 |
| 5 | 14 | 40 | 16 | 57 | 5.2 |
| 6 | 14 | 160 | 16 | 57 | 11.3 |
| 7 | 14 | 300 | 16 | 57 | 13.9 |
| 8[c] | 14 | 40 × 3 | 24 × 3 | 57 | 13.1 |

[a]Two mg of Pd catalyst, 6.4 μL HBF$_4$ were added to 300 μL H$_2$O except entries 2 and 3, whose reactions were run without additional H$_2$O addition.
[b]Turnover numbers were calculated by [CH$_3$CO$_2$H]/[Pd].
[c]40 μL of H$_2$O$_2$ and 400 psi CH$_4$ were added to the reactor every 24 hours for three days.

As shown in Table 8, the generation of acetic acid from methane is dependent upon oxidant concentration and 2,6-lutidine as stabilizer of peroxide, with higher reactivity observed using high content of hydrogen peroxide in the presence of 2,6-lutidine. Use of 40 μL hydrogen peroxide with 13 also exhibited low turnovers (entry 1); however, a larger quantity of this oxidant allowed for formation of acetic acid with 1.6 turnovers (entry 2). Additionally, use of catalyst 14 resulted in higher turnovers than reactions conducted in the presence 13 (entries 4~8), and inclusion of 2,6-lutidine in the reaction mixture lead to increased formation of acetic acid as well. Gas was generated rapidly when hydrogen peroxide was added to the reaction solutions containing 13, and this reactivity with the catalyst caused possible disproportionation of hydrogen peroxide, which may account for lower turnovers compared to reactions employing 14. Using 14, the turnovers were found to be dependent upon the amount of oxidant employed (entries 5-7) as increasing amounts of hydrogen peroxide used resulted in higher turnovers of acetic acid. When 40 μL of hydrogen peroxide was added every 24 hours over three days (entry 8), similar turnovers to a single addition of a larger quantity of hydrogen peroxide (entry 7) was obtained, which is the highest turnovers for direct formation of acetic acid from methane.

All articles, patents, patent applications, and other publications which have been cited in this disclosure are hereby incorporated herein by reference.

The present disclosure can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the disclosure. However, it should be recognized that the present disclosure can be practiced without resorting to the details specifically set forth. In other instances, well known processing structures have not been described in detail, in order not to unnecessarily obscure the present disclosure.

Only a few examples of the present disclosure are shown and described herein. It is to be understood that the disclosure is capable of use in various other combinations and environments and is capable of changes or modifications within the scope of the inventive concepts as expressed herein.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

The invention claimed is:

1. An N-Heterocyclic carbene-amido palladium(II) catalyst having a chemical structure according to general formula I:

wherein $R_1$ and $R_5$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms; $R_2$ is selected from the group consisting of H, alkyl of 1 to 10 carbon atoms, aryl of 1 to 10 carbon atoms, and aralkyl of 1 to 10 carbon atoms, or optionally forms part of a linkage to form a dimer; $R_3$ and $R_4$ is selected from the group consisting of H and an aryl ring of from 4 to 8 carbon atoms; $R_6$ is selected from the group consisting of H and alkoxy having 1-4 carbon atoms; and L is selected from the group consisting of a halogen or optionally forms part of a linkage to form a dimer, wherein the linkage from $R_1$ to the ring carbon is either chiral or achiral, and wherein the chemical structure may be in a dimeric form.

2. The N-Heterocyclic carbene-amido palladium(II) catalyst of claim 1, wherein the catalyst has a structure according to general formula II:

wherein $R_1$ and $R_2$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms.

3. The N-Heterocyclic carbene-amido palladium(II) catalyst of claim 1, wherein the catalyst has a structure according to general formula III:

wherein $R_1$ is selected from the group consisting of H, alkyl of 1 to 10 carbon atoms, aryl of 1 to 10 carbon atoms, and aralkyl of 1 to 10 carbon atoms, and may optionally contain one or more heteroatoms.

4. The N-Heterocyclic carbene-amido palladium(II) catalyst of claim 1, wherein the catalyst has a structure according to general formula IV:

wherein $R_1$ and $R_5$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms.

5. The N-Heterocyclic carbene-amido palladium(II) catalyst of claim 1, wherein the catalyst has a structure according to general formula V:

wherein $R_1$ and $R_2$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms.

6. The N-Heterocyclic carbene-amido palladium(II) catalyst of claim 1, wherein the catalyst has a structure according to general formula VI:

(VI)

wherein $R_1$ is selected from the group consisting of H, alkyl of 1 to 10 carbon atoms, aryl of 1 to 10 carbon atoms, and aralkyl of 1 to 10 carbon atoms, and may optionally contain one or more heteroatoms.

7. A method of forming a bond between a carbon atom and a second atom, wherein the method involves the step of contacting a first reactant containing the carbon atom and a second reactant containing the second atom in the presence of an N-Heterocyclic carbene-amido palladium(II) catalyst having a general formula (I):

(I)

where $R_1$ and $R_5$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms; $R_2$ is selected from the group consisting of H, alkyl of 1 to 10 carbon atoms, aryl of 1 to 10 carbon atoms, and aralkyl of 1 to 10 carbon atoms, or optionally forms part of a linkage to form a dimer; $R_3$ and $R_4$ is selected from the group consisting of H and aryl ring of from 4 to 8 carbon atoms; $R_6$ is selected from the group consisting of H and alkoxy of 1-4 carbon atoms; and L is selected from the group consisting of a halogen or optionally forms part of a linkage to form a dimer, wherein the linkage from $R_1$ to the ring carbon is either chiral or achiral, and wherein the chemical structure may be in a dimeric form.

8. The method of claim 7, wherein the second atom is carbon, the second reactant is an aryl boronic acid and wherein the catalyst has a structure according to general formula III:

(III)

wherein $R_1$ is selected from the group consisting of H, alkyl of 1 to 10 carbon atoms, aryl of 1 to 10 carbon atoms, and aralkyl of 1 to 10 carbon atoms, and may optionally contain one or more heteroatoms.

9. The method of claim 8, wherein $R_1$ is isopropyl.

10. The method of claim 8, wherein $R_1$ is phenyl.

11. The method of claim 7, wherein the second atom is oxygen, the second reactant is an acetic acid and wherein the catalyst has a structure according to general formula II:

(II)

wherein $R_1$ and $R_2$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms.

12. The method of claim 11, wherein $R_1$ is isopropyl and $R_2$ is benzyl.

13. The method of claim 7, wherein the second atom is nitrogen, the second reactant is an $NH_2SO_2Ph$ and wherein the catalyst has a structure according to general formula V:

(V)

wherein $R_1$ and $R_2$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms.

14. The method of claim 13, wherein $R_1$ is H and $R_2$ methyl.

15. The method of claim 7, wherein the second atom is deuterium, the second reactant is $D_2O$ and wherein the catalyst has a structure according to general formula V:

(V)

wherein $R_1$ and $R_2$ may be the same or different and are selected from the group consisting of H, alkyl of 1 to 10 carbon atoms, aryl of 1 to 10 carbon atoms, and aralkyl of 1 to 10 carbon atoms, and may optionally contain one or more heteroatoms
and the method further includes the presence of hydrogen peroxide.

16. The method of claim 15, wherein $R_1$ is H and $R_2$ methyl.

17. The method of claim 7, wherein the second atom is nitrogen, the second reactant is a primary amine and wherein the catalyst has a structure according to general formula VI:

(VI)

wherein $R_1$ is selected from the group consisting of H, alkyl of 1 to 10 carbon atoms, aryl of 1 to 10 carbon atoms, and aralkyl of 1 to 10 carbon atoms, and may optionally contain one or more heteroatoms.

18. The method of claim 17, wherein $R_1$ is isopropyl.

* * * * *